United States Patent [19] [11] 3,988,468
Rogalski et al. [45] Oct. 26, 1976

[54] 7-METHOXY-6-THIATETRACYCLINES AND THEIR PREPARATION

[75] Inventors: Werner Rogalski; Richard Kirchlechner; Juergen Seubert; Rudolf Gottschlich, all of Darmstadt; Walter Hameister, Brauweiler; Rolf Bergmann; Helmut Wahlig, both of Darmstadt, all of Germany

[73] Assignee: Merck Patent Gesellschaft mit beschrankter Haftung, Darmstadt, Germany

[22] Filed: July 30, 1975

[21] Appl. No.: 600,377

[30] Foreign Application Priority Data
Aug. 3, 1974 Germany............................ 2437487

[52] U.S. Cl. ............................... 424/275; 260/328
[51] Int. Cl.² ...................................... C07D 335/04
[58] Field of Search .................... 260/328, 345.3; 424/275

[56] References Cited
UNITED STATES PATENTS
3,901,942  8/1975  Bernardi et al. ............. 260/559 AT Primary Examiner—Natalie Trousof
Assistant Examiner—C. M. S. Jaisle
Attorney, Agent, or Firm—Millen, Raptes & White

[57] ABSTRACT

7-Methoxy-6-thiatetracyclines of the formula

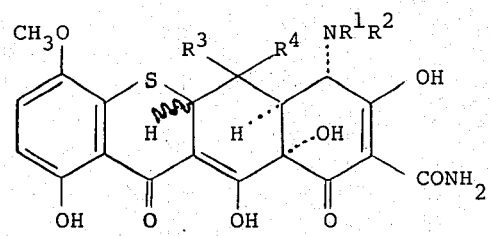

wherein $R^1$, $R^2$, $R^3$ and $R^4$ each are H or alkyl of 1 to 4 carbon atoms, and the physiologically acceptable acid addition salts thereof.

19 Claims, No Drawings

7-METHOXY-6-THIATETRACYCLINES AND THEIR PREPARATION

BACKGROUND OF THE INVENTION

This invention relates to novel tetracyclines and to processes for their production and use.

Carbocyclic tetracyclines have been prepared by total synthesis (cf., f.e., German Offenlegungsschrift 1,543,221). No heterocyclic tetracycline analogues (wherein a carbon atom of the tetracyclic system is replaced by a hetero atom, f.e. O or S) is known thus far.

SUMMARY OF THE INVENTION

In one composition aspect, this invention relates to novel 7-methoxy-6-thiatetracyclines of the general Formula I wherein $R^1$, $R^2$, $R^3$ and $R^4$ each are H or alkyl of 1 to 4 carbon atoms, and the physiologically acceptable acid addition salts thereof.

In another composition aspect, this invention relates to pharmaceutical compositions comprising a novel tetracycline of this invention.

In process aspects, this invention relates to a process for the production and for the use as antibacterial agents of the novel tetracyclines of this invention.

DETAILED DISCUSSION

The term "6-thiatetracycline" as used herein means 4-dimethylamino-1,4,4a,5,5a,6,11,12a-octahydro-3,10,12,12a-tetrahydroxy-1,11-dioxo-6-thia-naphthacene-2-carboxamide.

The compounds of Formula I and their physiologically acceptable acid salts possess valuable pharmacological properties with good toleration. For example, they exhibit a broad spectrum of antibacterial activity against both Gram-positive and Gram-negative bacteria, including tetracycline-resistant Gram-positive and Gram-negative organisms.

Accordingly, the novel tetracyclines of this invention can be used as medicines, especially as broad spectrum antibiotics for combating bacterial infections. They can also be used as intermediate products for the preparation of other medicines.

Preferred 7-methoxy-6-thiatetracyclines of Formula I and their physiologically acceptable acid addition salts are those wherein a. $R^1$, $R^2$, $R^3$ and $R^4$ are preferably H or methyl, but can also be ethyl, n-propyl, isopropyl, n-butyl, isobutyl, sec.-butyl or tert.-butyl;

b. $R^1$ and $R^2$ are preferably identical, especially those of (a); and c. $R^3$ and $R^4$ both are preferably H, especially those of (a) and (b).

Formula I can possess various stereochemical configurations. In particular, they can possess the same stereochemical configuration at the carbon atoms $C_{4a}$ and $C_{5a}$ of the tetracycline structure as the tetracyclines which are prepared by means of micro-organisms and in which the hydrogen atoms are in the syn-position ("natural configuration"). However, the carbon atoms $C_{4a}$ and $C_{5a}$ can carry hydrogen in the anti-position and thus possess an "unnatural configuration". Compounds having this "unnatural configuration" are designated herein as "5a-epi-compounds".

In a process aspect, this invention relates to a process for the preparation of the compounds of Formula I and of their physiologically acceptable acid addition salts, wherein a. a compound otherwise corresponding to those of Formula I but wherein at least one hydroxyl or amino group is present in a functionally modified form, is treated with solvolysing or hydrogenolysing agents, or b. a compound of the general Formula II wherein $R^1$ to $R^4$ have the values given above, is treated with a hydroxylating agent to introduce an hydroxy group at the 12a position; and optionally thereafter a primary or secondary amino group in a thus-produced compound is alkylated by treatment with an alkylating agent and/or that optionally a free base of Formula I is converted, by treatment with an acid, into a physiologically acceptable acid addition salt thereof.

In other respects, the preparation of the compounds of Formula I is carried out in accordance with conventional methods, such as are described in the literature (for example, in the standard works, such as Houben-Weyl, Methoden der Organischen Chemie (Methods of Organic Chemistry), Georg-Thieme Verlag, Stuttgart, and especially in the literature which is concerned with the chemistry of the tetracyclines), and in particular under the reaction conditions which are known and suitable for the reactions mentioned.

If desired, all the starting compounds for the preparation of the compounds of Formula I can also be formed in situ and are not isolated from the reaction mixture but are reacted further direct to give a compound of Formula I.

The starting materials are novel but they can be prepared by total synthesis, analogously to the methods known from the literature.

Amongst those starting materials which otherwise correspond to the general Formula I are those wherein at least one hydroxyl or amino group is present in a functionally modified form. Those in which the 4-amino group and/or the 10-hydroxyl group is functionally modified are preferred.

For example, the $NH_2$ radical of the carbamoyl group in the 2-position can be functionally modified. Also, the 4-amino group can preferably be modified in the form of an acyl or thioacyl derivative or of an imino-ether or imino-thioether derived therefrom. Accordingly, it is preferably present in the form of one of the groups $-NR^1-CY-R^5$ or $-N=C(YR^6)-R^5$, wherein $R^5$ is, e.g., H, alkyl with 1–10 carbon atoms or an unsubstituted phenyl, benzyl, phenoxymethyl or phenoxypropyl radical, or a phenyl, benzyl, phenoxymethyl or phenoxypropyl radical which is monosubstituted or disubstituted by alkyl with 1–4 carbon atoms, OH, temporarily protected OH, CH$_2$OH with an optionally temporarily protected OH group, NO$_2$, NH$_2$, alkylamino, dialkylamino, hydroxyalkylamino, acylamino, halogen, COOH, COOalkyl, CONH$_2$ or CONHalkyl; Y is an oxygen atom or a sulphur atom; and $R^6$ is alkyl, preferably of up to 4 carbon atoms. The acyl groups preferably are of up to 7 carbon atoms.

If the 10-hydroxyl group is functionally modified, it is preferably present in the form of a $R^7O$ group, wherein $R^7$ is alkyl, alkoxymethyl or acyl, each of which has preferably up to 5 carbon atoms, tetrahydropyranyl, carbobenzoxy or, especially, benzyl.

If the carbamoyl group in the 2-position is functionally modified, it is preferably present in the form of the radical $-CONHR^8$, wherein $R^8$ is alkyl of 1–6 carbon atoms, especially tert.-butyl.

The solvolytic splitting of a functionally modified hydroxyl and/or amino group must, of course, be carried out under such mild conditions that other groups in the molecule, for example, the carbamoyl group in the 2-position, are not also attacked. However, this is easily possible in accordance with procedures given in the literature. The solvolysis is preferably effected with the aid of an acid, for example, a mineral acid, e.g., hydrochloric acid, hydrobromic acid, sulphuric acid and phosphoric acid, an organic carboxylic acid, e.g., acetic acid, or a sulphonic acid, e.g., methanesulphonic acid and p-toluenesulphonic acid. Lewis acids, such as BF$_3$ and BBr$_3$, are also suitable for splitting functionally modified hydroxyl groups. The solvolysis can be carried out in the presence or absence of an inert solvent. Examples of suitable solvents are water, alcohols, e.g., methanol, ethanol and isopropanol, ethers, e.g., diethyl ether, tetrahydrofuran (THF) and dioxan, chlorinated hydrocarbons, e.g., methylene chloride, chloroform and trichloroethylene, hydrocarbons, e.g., benzene, or mixtures of these solvents. It is also possible to use an excess of the acid, for example acetic acid, as the solvent. Ordinarily, the solvolysis is carried out at temperatures of 0° to 150°, preferably 20° to 100°.

As an example, a N-substituted carbamoyl group in the 2-position, preferably a $-CO-NH$-tert.-butyl group, can be converted into the group $-CONH_2$ by treatment with HCl, HBr, sulphuric acid or phosphoric acid. The use of HBr in acetic acid at temperatures of 20° to 80° is particularly advantageous.

Hydrolysis of an amide group in the 4-position is effected particularly easily when $R^5$ is alkyl or a phenyl radical which is substituted at least in the o-position, in which case the substituent on the phenyl nucleus should facilitate the hydrolysis by an "adjacent group effect". The hydrolysis occurs even under very mild conditions, for example, in a weakly acid medium using dilute acetic acid, methanol, ethanol, THF and dioxan being preferred, as well as water, as additional inert solvents.

A specific procedure for eliminating acyl or thioacyl groups at the N atom in the 4-position is to convert them into the corresponding imino-ether or imino-thioether groups. This is preferably effected using alkylating agents such as methyl iodide and dimethyl sulphate, oxonium salts, such as triethyloxonium tetrafluoborate, or fluorosulphonic acid alkyl esters, such as fluorosulphonic acid methyl ester and fluorosulphonic acid ethyl ester. Preferably, the alkylating agent and the amide or thioamide to be split are allowed to act on one another in one of the inert solvents mentioned, for example in methanol, THF or methylene chloride. It is preferable for a base, such as KHCO$_3$ or bis-dimethylamino-naphthalene, to be present to neutralize the acid which is formed. The imino-ether or imino-thioether is then split by the action of one of the acids mentioned, preferably dilute acetic acid or dilute hydrochloric acid at temperatures of about 0° to 50°.

Hydroxyl and/or amino groups, which are protected by groups which can be split off hydrogenolytically, can thus be regenerated by hydrogenolysis. Thus, for example, O-benzyl, N-benzyl or carbobenzoxy groups can be removed and the imino-ethers or imino-thioethers mentioned, in which $R^5$ is a phenyl group, which is optionally substituted as indicated, can be split by hydrogenolysis.

The hydrogenolysis is preferably carried out in the presence of one of the customary metal catalysts, for example, in the presence of platinum, palladium, nickel or cobalt. These catalysts can be present as finely divided metals, as oxide catalysts (for example, platinum oxide) or on supports (for example, platinum or palladium on charcoal or palladium on calcium carbonate). The hydrogenolysis is appropriately carried out at pressures of 1 to 100 atmospheres and at temperatures of −80° to +150° in the presence of one of the indicated solvents, preferably at pressures of 1 to 10 atmospheres and temperatures of 20° to 50°, in methanol or ethanol.

Compounds of Formula I can also be produced by hydroxylation of compounds of Formula II in the 12-a position. A suitable and preferred hydroxylating agent is oxygen, which is preferably used in the presence of a metal or metal salt oxidation catalyst (for example, PtO$_2$ or CeCl$_3$), under alkaline conditions, for example, in the presence of a buffer solution, and in the presence of one of the inert solvents mentioned, preferably methanol, ethanol, THF, dimethylformamide (DMF) and/or water. The reaction temperatures for the hydroxylation are preferably 0° to 50°, especially 20° to 30°, and the reaction times are, e.g., 1 to 24 hours, preferably 4 to 12 hours.

If desired, a primary or secondary amine of Formula I ($R^1$ and/or $R^2$ = H) can be alkylated, by treatment with an alkylating agent, to give the corresponding secondary or tertiary amine.

Examples of suitable alkylating agents are alkyl halides, e.g., methyl chloride, methyl bromide, methyl iodide, ethyl chloride, ethyl bromide and ethyl iodide, dialkyl sulphates, e.g., dimethyl sulphate and diethyl sulphate, alcohols, e.g., methanol and ethanol, in the presence of Raney nickel, or the corresponding aldehydes or ketones, e.g., formaldehyde, acetaldehyde and acetone, in the presence of a reducing agent, for example, in the presence of hydrogen and a metal catalyst, or of formic acid, or in the presence of a complex metal hydride, e.g., as sodium cyanoborohydride. Preferred solvents for the alkylation are alcohols, e.g., methanol and ethanol, ether-alcohols, e.g., 2-methoxyethanol and 2-ethoxyethanol, ethers, e.g., THF and dioxan, or amides, e.g., DMF.

The alkylation can also be carried out in two stages. For example, a primary amine of Formula I can first be acylated, for example converted into the corresponding formyl derivative using the mixed anhydride of formic acid and acetic acid (for example, in formic acid in the presence of sodium formate). The resulting acyl derivative can then be converted into the desired secondary amine, for example, by catalytic hydrogenation under the conditions described above.

It is, of course, possible and in some cases advantageous, to combine two or even more of the process measures described with one another.

Thus, for example, the amino group in the 4-position and the hydroxyl group in the 10-position can simultaneously be liberated hydrolytically from corresponding derivatives by using, for example HBr, HI or $BF_3$ as the agent. It is also possible, for example, simultaneously to carry out hydrogenolytic splitting of a benzyloxy group, present on the $C_{(10)}$ atom, and reductive alkylation of an amino group in the 4-position, in the presence of hydrogen and a catalyst.

A base of Formula I can be converted into one of its physiologically acceptable acid addition salts by treatment with an acid, preferably under anhydrous conditions. Acids which can be used for this reaction are inorganic acids, for example, sulphuric acid, nitric acid, hydrogen halide acids, e.g., hydrochloric acid, hydrobromic acid and hydriodic acid, and phosphoric acids, e.g., orthophosphoric acid, as well as organic acids, especially aliphatic, alicyclic, araliphatic, aromatic or heterocyclic monobasic or polybasic carboxylic acids or sulphonic acids, such as formic acid, oxalic acid, malonic acid, succinic acid, pimelic acid, fumaric acid, maleic acid, tartaric acid, malic acid, gluconic acid, citric acid, methanesulphonic acid or ethanesulphonic acid, ethanedisulphonic acid, 2-hydroxyethanesulphonic acid, benzenesulphonic acid, p-toluenesulphonic acid or naphthalene-monosulphonic acids or naphthalene-disulphonic acids (for example naphthalene-1- or -2-sulphonic acid or naphthalene-1,5- or -2,6-disulphonic acid). Other acids can be employed for isolation, purification or characterization purposes.

The compounds of Formula I and their physiologically acceptable acid addition salts can be used as medicaments in human medicine or veterinary medicine, e.g., mixed with solid, liquid and/or semi-liquid medicinal excipients, e.g., organic or inorganic substances which are suitable for enteral, parenteral or topical administration and which do not react with the new compounds, such as, for example, water, vegetable oils, polyethylene glycols, gelatine, lactose, starch, magnesium stearate, talc and white petroleum jelly. Tablets, dragees, capsules, syrups, elixirs or suppositories, for example are suitable for enteral administration. Solutions, preferably oily or aqueous solutions, and suspensions, emulsions or implants, are in particular used for parenteral administration and ointments, creams or powders are used for topical administration. These preparations can be sterilized and/or contain auxiliaries, such as preservatives, stabilizers and/or wetting agents, salts for regulating the osmotic pressure, buffer substances, dyestuffs, flavorings and/or scents. If desired, they can also contain one or more other active substances, for example vitamins, such as vitamin $B_1$, $B_2$, $B_6$, $B_{12}$ and C.

As a rule, the novel tetracyclines of this invention are administered analogously to the known tetracyclines, such as tetracycline, chlorotetracycline or hydroxytetracycline, preferably in doses of about 10 to about 1,000, e.g., 50 and 500 mg per dosage unit. The daily dose is preferably 0.2 to 20 mg/kg of body weight. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Fluorosulphonic acid methyl ester of 0.3 g is added to a solution of 555 mg of 4-de-dimethylamino-4-thiobenzamido-7-methoxy-6-thiatetracycline (4-thiobenzamido-1,4,4a,5,5a,6,11,12a-octahydro-3,10,12,12a-tetrahydroxy-7-methoxy-1,11-dioxo-6-thianaphthacene-2-carboxamide) and 850 mg of 1,8-bis-dimethylaminonaphthalene in a mixture of 50 ml of methylene chloride and 50 ml of methanol and the mixture is stirred under nitrogen for 25 minutes at 20°. The corresponding S-methyl-imino-thio ether is formed. The mixture is then stirred in water and extracted with chloroform and the extracts are washed several times with dilute hydrochloric acid, dried and evaporated. The residue is dissolved in THF, 1 N hydrochloric acid is added and the mixture is stirred for 1 hour at 20°. The THF is then distilled off and the residual aqueous solution, which contains hydrochloric acid, is extracted with butanol and the extract is evaporated. This gives 4-de-dimethylamino-4-amino-7-methoxy-6-thiatetracycline (4-amino-1,4,4a,5,5a,6,11,12a-octahydro-3,10,12,12a-tetrahydroxy-7-methoxy-1,11-dioxo-6-thianaphthacene-2-carboxamide), m.p. above 270°.

The starting material for the above reaction can be obtained as follows:

a. 16 g of 2,5-dimethoxybenzene-sulphonyl chloride are dissolved in 100 ml of THF, while stirring, and a mixture of 20 ml of concentrated $H_2SO_4$ and 60 ml of water is then added, followed by 25 g of zinc dust, added in portions at 50°–55° and stirring is continued overnight at 20°. The THF is then stripped off and the mixture is worked up with water and methylene chloride to give 2,5-dimethoxythiophenol, b.p. 106°–108°/0.3 mm.

b. A mixture of 25.5 g of 2,5-dimethoxythiophenol and 2 ml of 10% sodium methylate solution (obtained by dissolving 70 mg of sodium in 2 ml of methanol) is warmed to 60° and 26.1 g of glutaconic acid dimethyl ester are added dropwise at 60°–80°, while stirring. The mixture is then heated at 80° for a further hour, while stirring, and the product is poured into half-concentrated hydrochloric acid and boiled for 8 hours. On cooling, 3-(2,5-dimethoxyphenylmercapto)-glutaric acid precipitates; m.p. 135°–137°.

c. 36 g of this acid are allowed to stand for 3 days at room temperature with 100 g of hydrogen fluoride and the mixture is poured onto ice and filtered to give 5,8-dimethoxy-thiochroman-4-one-2-acetic acid; m.p. 183°–184°.

d. 26.8 g of the above acid are suspended in 300 ml of chloroform and 21.6 g of $PCl_5$ are introduced at 5°–10°. The mixture is stirred for a further hour, the solvent is removed and the resulting crude acid chloride is dissolved in 50 ml of dioxan. The resulting solution is stirred slowly into 220 ml of a 33% aqueous $NH_3$ solution to give 5,8-dimethoxy-thiochroman-4-one-2-acetamide; m.p. 202°–204°.

e. 25.7 g of p-toluenesulphochloride are added to a suspension of 25.3 g of the amide in 40 ml of pyridine, while stirring, and the mixture is stirred overnight, poured onto ice and worked up with chloroform and aqueous hydrochloric acid to give 5,8-dimethoxy-thiochroman-4-one-2-acetonitrile; m.p. 132°–134°.

f. A solution of 2 ml of BBr$_3$ in 10 ml of methylene chloride is added dropwise at −60° to −50° to a solution of 5.3 g of the nitrile in 60 ml of methylene chloride, and the mixture is allowed to warm to +10°, while continuing to stir. The mixture is poured onto ice and worked up to give 5-hydroxy-8-methoxy-thiochroman-4-one-2-acetonitrile; m.p. 126°–127° C.

g. A solution of 28 g of Na$_3$PO$_4$.12H$_2$O in 24 ml of water and 60 ml of acetic acid is added to a solution of 2.49 g of the nitrile in 24 ml of pyridine. 22 g of Raney nickel are then added and the mixture is stirred for 20 minutes, the catalyst is filtered off and the filtrate is worked up with dilute hydrochloric acid and chloroform to give 5-hydroxy-8-methoxy-thiochroman-4-one-2-acetaldehyde; m.p. 92°–94°.

h. 7.56 g of the above aldehyde are dissolved in 90 ml of absolute THF, 24 g of MgSO$_4$ and 10.8 g of Pb(OOCCH$_3$)$_2$ are added to the solution, a solution of 4.78 g of 2-phenyl-2-thiazolin-5-one in 30 ml of THF is then added dropwise while stirring and passing in nitrogen. The mixture is then stirred for another 5 minutes. The inorganic salts are filtered off, the filtrate is evaporated and the residue is treated with acetone, from which 2-phenyl-4-[2-(5-hydroxy-8-methoxy-thiochroman-4-on-2-yl)-ethylidene]-2-thiazolin-5-one crystallizes; m.p. 171°–172°.

i. 8.23 g of the above thiazolinone and 3.5 g of acetone-dicarboxylic acid monomethyl ester-monoamide are dissolved in a mixture of 100 ml of pyridine and 34 ml of DMF. 0.72 g of NaH is then added, while passing in nitrogen, and the mixture is stirred for 2 hours while continuing to pass in nitrogen. A further 0.96 g of NaH is then added and the mixture is heated to the boil. After boiling for 20 minutes, a further 0.24 g of NaH is added and the mixture is boiled for a further 30 minutes. After cooling, methanol is added and the mixture is poured onto a mixture of hydrochloric acid and ice and worked up with chloroform to give an amorphous mixture of stereoisomeric 4-thiobenzamido-1,4,4a,5-,5a,6,11,12a-octahydro-3,10,12-trihydroxy-7-methoxy-1,11-dioxo-6-thianaphthacene-2-carboxamides. The crude product is dissolved in 100 ml of piperidine and stirred for 3½ hours at 20°, while passing nitrogen through the solution, in order to epimerize it at C$_{(4)}$. The solution is then stirred into a mixture of hydrochloric acid and ice water and the solution thus obtained is then stirred into chloroform. After working up, the residue obtained from the organic phase is triturated with petroleum ether and the insoluble fraction is filtered off and dissolved in acetone, from which 4-de-dimethylamino-4-thiobenzamido-7-methoxy-12a-dehydroxy-6-thiatetracycline crystallizes; m.p. 253°–154°.

j. 2 g of the above 6-thiatetracycline are dissolved in 100 ml of DMF and the solution is treated with 240 ml of THF and then, while stirring, with 1.2 g of fine NaH. While continuing to stir, oxygen is passed through the solution and, in the early part of this period, about 0.4 ml of water is sprayed in below the surface using a syringe. After 4 hours, the reaction mixture is stirred into dilute hydrochloric acid. The mixture is extracted with ethyl acetate and worked up and the produce is purified chromatographically on silica gel (elution agent, chloroform) to give 4-de-dimethylamino-4-thiobenzamido-7-methoxy-6-thiatetracycline; m.p. 223° (from acetone).

EXAMPLE 2

Analogously to Example 1, 4-de-dimethylamino-4-amino-7-methoxy-5a-epi-6-thiatetracycline is obtained from 4-de-dimethylamino-4-thiobenzamido-7-methoxy-5a-epi-6-thiatetracycline by reaction with fluorosulphonic acid methyl ester to give the corresponding S-methyl-imino-thioether and subsequent hydrolysis with hydrochloric acid.

The starting material can be obtained from the filtrate which results after 4-de-dimethylamino-4-thiobenzamido-7-methoxy-12a-dehydroxy-6-thiatetracycline has been filtered from the acetone solution (compare Example 1, paragraph i) by isolating the corresponding 5a-epi compound and hydroxylating this in the 12a-position.

EXAMPLE 3

Analogously to Example 1, 4-de-dimethylamino-4-amino-5-methyl-7-methoxy-6-thiatetracycline is obtained from 4-de-dimethylamino-4-thiobenzamido-5-methyl-7-methoxy-6-thiatetracycline.

The starting material can be obtained by condensation of 2,5-dimethoxythiophenol with 2-methylglutaconic acid dimethyl ester to give 2-methyl-3-(2,5-dimethoxyphenylmercapto)-glutaric acid, cyclisation to give 2-(5,8-dimethoxy-thiochroman-4-one-2-yl)-propionic acid (some 3-methyl-5,8-dimethoxy-thiochroman-4-one-2-acetic acid is also formed during the cyclisation and is separated off chromatographically), successive conversion into the acid chloride, the amide and the nitrile and splitting of the ether to give 2-(5-hydroxy-8-methoxy-thiochroman-4-one-2-yl)-propionitrile, reaction to give the aldehyde and condensation with 2-phenyl-2-thiazolin-5-one to give 2-phenyl-4-[2-(5-hydroxy-8-methoxy-thiochroman-4-on-2-yl)-propylidene]-2-thiazolin-5-one, condensation with acetone-dicarboxylic acid monomethyl ester-monamide to give a mixture of stereoisomeric 4-thiobenzamido-1,4,4a,5,5a,6,11,12a-octahydro-3,10,12-trihydroxy-7-methoxy-5-methyl-1,11-dioxo-6-thianaphthacene-2-carboxamides, epimerization with piperidine to give 4-de-dimethylamino-4-thiobenzamido-5-methyl-7-methoxy-12a-dehydroxy-6-thiatetracycline and hydroxylation.

4-De-dimethylamino-4-amino-5-ethyl-7-methoxy-6-thiatetracycline,
4-de-dimethylamino-4-amino-5-n-propyl-7-methoxy-6-thiatetracycline,
4-de-dimethylamino-4-amino-5-n-butyl-7-methoxy-6-thiatetracycline,
4-de-dimethylamino-4-amino-5,5-dimethyl-7-methoxy-6-thiatetracycline,
4-de-dimethylamino-4-amino-5-methyl-5-ethyl-7-methoxy-6-thiatetracycline and
4-de-dimethylamino-4-amino-5,5-diethyl-7-methoxy-6-thiatetracycline
can be obtained analogously from the corresponding starting materials alkylated in the 5-position.

The hydrochlorides of each of the above free bases can be produced by dissolving the base in ethyl acetate (about 200 ml. per g. base), introducing an excess of gaseous hydrogen chloride and evaporation to dryness.

EXAMPLE 4

20 ml of 6 N hydrochloric acid are added to a solution of 462 mg of 4-de-dimethylamino-4-formamido-7-methoxy-6-thiatetracycline (obtainable from 4-de-dimethylamino-4-thiobenzamido-7-methoxy-12a-dehydroxy-6-thiatetracycline by solvolysis to give the 4-amino compound, formylation to give 4-de-dimethylamino-4-formamido-7-methoxy-12a-dehydroxy-6-thiatetracycline and oxidation with $O_2$/NaH) in 20 ml of dioxane and the solution is heated at 50° for 2 hours, diluted with water and extracted with butanol. The extract is dried and evaporated to give 4-de-dimethylamino-4-amino-7-methoxy-6-thiatetracycline; m.p. above 270°.

EXAMPLE 5

476 mg of 7-methoxy-10-O-methyl-6-thiatetracycline (4-dimethylamino-1,4,4a,5,5a,6,11,12a-octahydro-3,12,12a-trihydroxy-7,10-dimethoxy-1,11-dioxo-6-thianaphthacene-2-carboxamide) are heated for 15 minutes at 100° with 5 ml of a 40% solution of HBr in acetic acid, the mixture is poured into water and extracted with n-butanol and 7-methoxy-6-thiatetracycline (4-dimethylamino-1,4,4a,5,5a,6,11,12a-octahydro-3,10,12,12a-tetrahydroxy-7-methoxy-1,11-dioxo-6-thianaphthacene-2-carboxamide) is obtained after conventional working up; m.p. 225°.

The starting material can be prepared from 5,8-dimethoxy-thiochroman-4-one-2-acetonitrile via 5,8-dimethoxy-thiochroman-4-one-2-acetaldehyde, 2-phenyl-4-[2-(5,8-dimethoxy-thiochroman-4-on-2-yl)-ethylidene]-2-thiazolin-5-one, 4-de-dimethylamino-4-thiobenzamido-7-methoxy-10-O-methyl-12a-dehydroxy-6-thiatetracycline, 4-de-dimethylamino-4-thiobenzamido-7-methoxy-10-O-methyl-6-thiatetracycline and 4-de-dimethylamino-4-amino-7-methoxy-10-O-methyl-6-thiatetracycline.

EXAMPLE 6

A solution of 100 mg of 7-methoxy-10O-benzyl-6-thiatetracycline (10-benzyloxy-4-dimethylamino-1,4,4a,5,5a,6,11,12a-octahydro-3,12,12a-trihydroxy-7-methoxy-1,11-dioxo-6-thianaphthacene-2-carboxamide) in 25 ml of methanol is hydrogenated at 20° and 1 atmosphere on 50 mg of 5% Pd-on-charcoal until the adsorption of $H_2$ has ceased. The mixture is filtered and the filtrate evaporated to give 7-methoxy-6-thiatetracycline; m.p. 225°.

EXAMPLE 7

A mixture of 518 mg of $N_{(2)}$-tert.butyl-7-methoxy-6-thiatetracycline, 10 ml of 48% HBr and 15 ml of acetic acid is heated at 100° for 15 minutes. After working up with water and n-butanol, 7-methoxy-6-thiatetracycline is obtained; m.p. 225°.

The starting material can be obtained by condensation of 2-phenyl-4-[2-(5-hydroxy-8-methoxy-thiochroman-4-on-2-yl)-ethylidene]-2-thiazolin-5-one with acetonedicarboxylic acid monomethyl ester-mono-N-tert.-butylamide to give a mixture of stereoisomeric 4-thiobenzamido-1,4,4a,5,5a,6,11,12a-octahydro-3,10,12-trihydroxy-7-methoxy-1,11-dioxo-6-thianaphthacene-2-N-tert.-butyl-carboxamides, epimerization with piperidine to give $N_{(2)}$-tert.butyl-4-de-dimethylamino-4-thiobenzamido-7-methoxy-12a-dehydroxy-6-thiatetracycline, hydroxylation to give $N_{(2)}$-tert.-butyl-4-de-dimethylamino-4-thiobenzamido-7-methoxy-6-thiatetracycline, reaction with fluorosulphonic acid methyl ester to give the methyliminothioether, hydrolysis to the 4-amino compound (analogously to Example 1) and methylation analogously to Example 9.

EXAMPLE 8

200 mg of 7-methoxy-12a-dehydroxy-6-thiatetracycline are dissolved in 150 ml of methanol and a solution of 175 mg of Cer(III) chloride in 85 of methanol is added to the solution while stirring. 2.35 ml of a buffer solution (prepared from 38.3 ml of 0.1 N NaOH and 61.7 ml of an aqueous solution which contains 7.505 g of glycine and 5.85 g of NaCl per liter) are added to the resulting mixture. Oxygen is then passed through the mixture for 12 hours and the solution is then concentrated to about 50 ml and worked up with hydrochloric acid and chloroform to give 7-methoxy-6-thiatetracycline; m.p. 225°.

The starting material can be prepared from 4-de-dimethylamino-4-thiobenzamido-7-methoxy-12a-dehydroxy-6-thiatetracycline by hydrolysis to give 4-de-dimethylamino-4-amino-7-methoxy-12a-dehydroxy-6-thiatetracycline and subsequent methylation.

EXAMPLE 9

400 mg of sodium cyanoborohydride, 0.5 ml of 35% aqueous formaldehyde solution and a little sodium sulphate are added to a solution of 434 mg of 4-de-dimethylamino-4-amino-7-methoxy-6-thiatetracycline (obtained in accordance with Example 1) in 80 ml of methanol and the mixture is stirred for 30 minutes at 20°. Chloroform is then added, followed by washing with dilute hydrochloric acid, drying and evaporation to give 7-methoxy-6-thiatetracycline, m.p. 225°.

5-methyl-7-methoxy-6-thiatetracycline,
5-ethyl-7-methoxy-6-thiatetracycline,
5-n-propyl-7-methoxy-6-thiatetracycline,
5-n-butyl-7-methoxy-6-thiatetracycline,
5,5-dimethyl-7-methoxy-6-thiatetracycline,
5-methyl-5-ethyl-7-methoxy-6-thiatetracycline and
5,5-diethyl-7-methoxy-6-thiatetracycline
can be obtained analogously by methylation.

EXAMPLE 10

434 mg of 4-de-dimethylamino-4-amino-7-methoxy-6-thiatetracycline and 0.5 ml of 35% aqueous formaldehyde solution are dissolved in 80 ml of methanol, 100 mg of 5% Pd-on-charcoal are added and the solution is hydrogenated at 20° and normal pressure until saturation is reached. After filtration and evaporation, 7-methoxy-6-thiatetracycline is obtained; m.p. 225°.

4-de-dimethylamino-4-diethylamino-7-methoxy-6-thiatetracycline,
4-de-dimethylamino-4-di-n-propylamino-7-methoxy-6-thiatetracycline,
4-de-dimethylamino-4-diisopropylamino-7-methoxy-6-thiatetracycline,
4-de-dimethylamino-4-di-n-butylamino-7-methoxy-6-thiatetracycline,
4-de-dimethylamino-4-diisobutylamino-7-methoxy-6-thiatetracycline and
4-de-dimethylamino-4-di-sec.-butylamino-7-methoxy-6-thiatetracycline
are obtained analogously using the corresponding aldehydes or ketones.

EXAMPLE 11 a. 471 mg of 4-de-dimethylamino-4-amino-7-methoxy-6-thiatetracycline hydrochloride (obtained in accordance with Example 1) are dissolved in 20 ml of formic acid, 0.95 g of the mixed anhydride of formic acid and acetic acid and 70 mg of sodium formate are added and the mixture is stirred for 24 hours at 20°. 4-de-dimethylamino-4-formamido-7-methoxy-6-thiatetracycline is obtained after evaporation; m.p. from 230° (decomposition).

b. 462 mg of 4-de-dimethylamino-4-formamido-7-methoxy-6-thiatetracycline are stirred with 400 mg of sodium cyanoborohydride in 80 ml of methanol for 1 hour at 20° and the mixture is worked up with dilute hydrochloric acid and chloroform to give 4-de-dimethylamino-4-methylamino-7-methoxy-6-thiatetracycline.

The examples which follow illustrate pharmaceutical preparations containing 7-methoxy-6-thiatetracyclines of this invention:

EXAMPLE A: Tablets

A mixture consisting of 100 kg of 7-methoxy-6-thiatetracycline, 500 kg of lactose, 170 kg of potato starch, 10 kg of magnesium stearate and 10 kg of talc is pressed in the conventional manner to give tablets each containing 100 mg of the tetracycline.

EXAMPLE B: Dragees

Tablets are pressed analogously to Example A and are subsequently coated in the customary manner with a coating consisting of sugar, potato starch, talc and tragacanth.

EXAMPLE C: Capsules 50 kg of 4-de-dimethylamino-4-amino-7-methoxy-6-thiatetracycline are filled into hard gelatine capsules in the customary manner, so that each capsule contains 50 mg of the active substance.

EXAMPLE D:

A pulverulent mixture consisting of 250 kg of 7-methoxy-6-thiatetracycline, 2.5 kg of finely disperse silicic acid, 12.5 kg of talc, 1.25 kg of magnesium stearate, 2.5 kg of vitamin $B_1$ chloride-hydrochloride, 2.5 kg of lactoflavin, 25 kg of nicotinamide, 0.5 kg of pyridoxine hydrochloride, 5 kg of calcium D-pantothenate, 4 kg of folic acid, 3 g of cyanocobalamine and 84 kg of sodium ascorbate is filled into hard gelatine capsules in the conventional manner to give capsules each containing 250 mg of the antibiotic.

Tablets, dragees and capsules which contain one or more of the other compounds of Formula I, or their physiologically acceptable salts, can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 7-methoxy-6-thiatetracycline of the formula

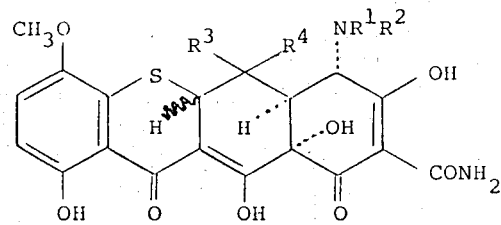

wherein $R^1$, $R^2$, $R^3$ and $R^4$ each are H or alkyl of 1 to 4 carbon atoms, and the physiologically acceptable acid addition salts thereof.

2. A compound of claim 1, wherein $R^1$, $R^2$, $R^3$ and $R^4$ each are H or methyl.

3. A compound of claim 1, wherein $R^1$ and $R^2$ are identical.

4. A compound of claim 2, wherein $R^3$ and $R^4$ are H.

5. A compound of claim 1, wherein the 5a hydrogen is in natural stereoconfiguration.

6. A compound of claim 5, wherein $R^1$, $R^2$, $R^3$ and $R^4$ each are H or methyl, and $R^1$ and $R^2$ are identical.

7. The 5a-epistereoisomers of claim 1.

8. A compound of claim 7, wherein $R^1$, $R^2$, $R^3$ and $R^4$ each are H or methyl and $R^1$ and $R^2$ are identical.

9. A compound of claim 1, 4-de-dimethylamino-4-amino-7-methoxy-6-thiatetracycline.

10. A compound of claim 1, 7-methoxy-6-thiatetracycline.

11. A compound of claim 1, 4-de-dimethylamino-4-amino-7-methoxy-5a-epi-6-thiatetracycline.

12. A compound of claim 1, 7-methoxy-5a-epi-6-thiatetracycline.

13. A pharmaceutical composition adapted for the treatment of bacterial infections comprising, in unit dosage form, an antibacterially effective amount per unit dosage of a compound of claim 1, in admixture with a pharmaceutically acceptable carrier.

14. A method of treating bacterial infections which comprises administering systemically to the infected patient a dosage of a compound of claim 1 effective to treat the infection.

15. A compound of the formula

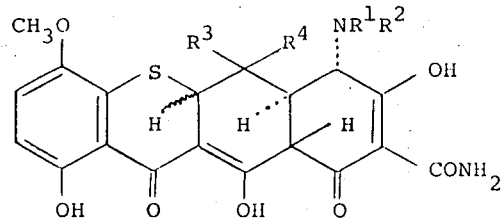

wherein $R^1$, $R^2$, $R^3$ and $R^4$ each are H or alkyl of 1–4 carbon atoms, and acid addition salts thereof.

16. A compound of claim 15, wherein $R^1$ and $R^2$ are identical.

17. A compound of claim 16, wherein $R^1$, $R^2$, $R^3$ and $R^4$ each are H or methyl.

18. A compound of claim 16, wherein $R^3$ and $R^4$ are H.

19. 4 de-dimethylamino-4-thiobenzamido-7-methoxy-12a-dehydroxy-6-thiatetracycline.

* * * * *